US010564234B2

(12) United States Patent
Driemel

(10) Patent No.: US 10,564,234 B2
(45) Date of Patent: Feb. 18, 2020

(54) HEAD/NECK LOCAL COIL WITH A NECK REGION WITH AUTOMATIC SIZE ADJUSTMENT WHEN TILTING THE HEAD/NECK LOCAL COIL

(71) Applicant: Daniel Driemel, Oederan (DE)

(72) Inventor: Daniel Driemel, Oederan (DE)

(73) Assignee: SIEMENS AKTIENGESELLSCHAFT, München (DE)

(*) Notice: Subject to any disclaimer, the term of this patent is extended or adjusted under 35 U.S.C. 154(b) by 1558 days.

(21) Appl. No.: 14/466,999

(22) Filed: Aug. 23, 2014

(65) Prior Publication Data
US 2015/0057528 A1 Feb. 26, 2015

(30) Foreign Application Priority Data
Aug. 23, 2013 (DE) .................. 10 2013 216 861

(51) Int. Cl.
G01R 33/34 (2006.01)
A61B 5/055 (2006.01)
G01R 33/36 (2006.01)
G01R 33/385 (2006.01)
G01R 33/483 (2006.01)

(52) U.S. Cl.
CPC ...... *G01R 33/34084* (2013.01); *A61B 5/0555* (2013.01); *G01R 33/3642* (2013.01); *G01R 33/385* (2013.01); *G01R 33/4833* (2013.01); *G01R 33/34046* (2013.01)

(58) Field of Classification Search
CPC ........ G01R 33/34084; G01R 33/34007; G01R 33/3642; G01R 33/4833; G01R 33/385; G01R 33/34046; A61B 5/0555
See application file for complete search history.

(56) References Cited

U.S. PATENT DOCUMENTS

| 6,980,002 | B1 | 12/2005 | Petropoulos et al. | |
| 2011/0260728 | A1* | 10/2011 | Biber | G01R 33/34061 324/318 |
| 2012/0286784 | A1* | 11/2012 | Driemel | G01R 33/34007 324/318 |
| 2013/0023756 | A1* | 1/2013 | Driemel | G01R 33/28 600/422 |
| 2013/0184563 | A1 | 7/2013 | Driemel | |

FOREIGN PATENT DOCUMENTS

| DE | 102004052943 A1 | 6/2005 |
| DE | 102011079565 A1 | 1/2013 |
| DE | 102011079575 A1 | 1/2013 |

OTHER PUBLICATIONS

German Office Action dated Apr. 14, 2014 in corresponding German Patent Application No. DE 10 2013 216 861.6 with English translation.

* cited by examiner

*Primary Examiner* — Carolyn A Pehlke
(74) *Attorney, Agent, or Firm* — Lempia Summerfield Katz LLC

(57) ABSTRACT

A head/neck local coil for an imaging magnetic resonance imaging system includes a head/neck local coil lower part that is tiltable with a tilting movement. The head/neck local coil also includes a neck part movable relative to the head/neck local coil lower part for compensating the tilting movement.

18 Claims, 11 Drawing Sheets

HEAD/NECK LOCAL COIL WITH A NECK REGION WITH AUTOMATIC SIZE ADJUSTMENT WHEN TILTING THE HEAD/NECK LOCAL COIL

This application claims the benefit of DE 10 2013 216 861.6, filed on Aug. 23, 2013, which is hereby incorporated by reference in its entirety.

BACKGROUND

The present embodiments relate to a local coil.

Magnetic resonance imaging (MRI) devices for examining objects or patients by magnetic resonance imaging are known from, for example, DE 10 2011 079 565.

SUMMARY

The scope of the present invention is defined solely by the appended claims and is not affected to any degree by the statements within this summary.

The present embodiments may obviate one or more of the drawbacks or limitations in the related art. For example, a local coil is optimized.

DETAILED DESCRIPTION

Figure 11:
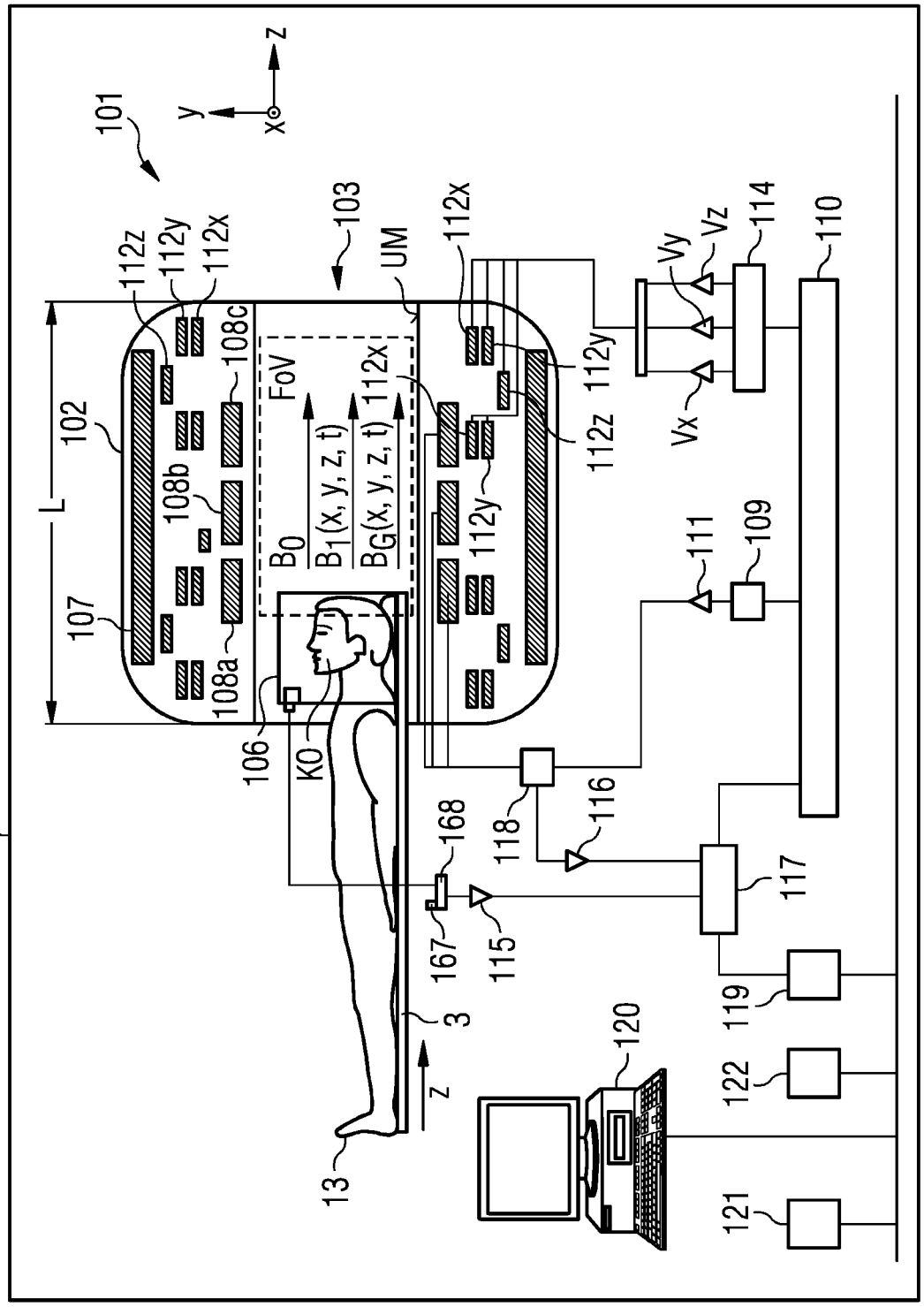
FIG. 11 shows one embodiment of a magnetic resonance imaging (MRI) system.

FIG. 11 shows a magnetic resonance imaging (MRI) device 101 (e.g., situated in a shielded room or Faraday cage F) with a whole body coil 102 with, for example, a tubular space 103 in which a patient couch 3 with a body of, for example, an examination object 13 (e.g., of a patient; with or without local coil arrangement 106) may be displaced in the direction of the arrow z in order to generate recordings of the patient 13 by an imaging method. In this case, the local coil arrangement 106 is arranged on the patient. Using the local coil arrangement, in a local region (e.g., field of view (FOV)) of the MRI, recordings of a portion of the body 13 in the FOV may be generated. Signals of the local coil arrangement 106 may be evaluated (e.g., converted into images, stored or displayed) by an evaluation device (e.g., including elements 168, 115, 117, 119, 120, 121, etc.) of the MRI 101, which may be connected to the local coil arrangement 106 using, for example, coaxial cables or by radio link (e.g., element 167).

In order to use an MRI device 101 to examine a body 13 (e.g., an examination object or a patient) using magnetic resonance imaging, different magnetic fields that are precisely matched to one another in terms of temporal and spatial characteristics are radiated onto the body 13. A strong magnet (e.g., a cryomagnet 107) in a measurement cabin with an opening 103 that is, for example, tunnel-shaped generates a strong static main magnetic field B0 that has a strength of, for example, 0.2 Tesla to 3 Tesla or more. A body 13 to be examined is, while supported by a patient couch 3, driven into a region of the main magnetic field B0 that is approximately homogeneous in the observation region FoV. The nuclear spins of atomic nuclei of the body 13 are excited by magnetic radiofrequency excitation pulses $B1(x, y, z, t)$ that are radiated in by a radiofrequency antenna (and/or, optionally, a local coil arrangement) that is depicted in FIG. 11 in a simplified manner as body coil 108 (e.g., multi-part body coil 108a, 108b, 108c). By way of example, radiofrequency excitation pulses are generated by a pulse generation unit 109 that is controlled by a pulse sequence control unit 110. After amplification by a radiofrequency amplifier 111, the radiofrequency excitation pulses are conducted to the radiofrequency antenna 108. The radiofrequency system shown in FIG. 11 is merely indicated schematically. In a magnetic resonance imaging device 101, more than one pulse generation unit 109, more than one radiofrequency amplifier 111, and a plurality of radiofrequency antennas 108 a, b, c may be used.

The magnetic resonance imaging device 101 also includes gradient coils $112x$, $112y$, $112z$, by which magnetic gradient fields $B_G$ (x, y, z, t) are radiated in during a measurement for selective slice excitation and for spatial encoding of the measurement signal. The gradient coils $112x$, $112y$, $112z$ are controlled by a gradient coil control unit 114 and, optionally, via amplifiers Vx, Vy, Vz that, like the pulse generation unit 109, is connected to the pulse sequence control unit 110.

Signals emitted by the excited nuclear spins (e.g., of the atomic nuclei in the examination object) are received by the body coil 108 and/or at least one local coil arrangement 106, amplified by associated radiofrequency preamplifiers 116 and processed further and digitized by a reception unit 117. The recorded measurement data is digitized and stored as complex numbers in a k-space matrix. An associated MR image may be reconstructed from the k-space matrix filled with values by a multidimensional Fourier transform.

For a local coil that may be operated both in transmission mode and in reception mode, such as, for example, the body coil 108 or a local coil 106, the correct signal transmission is regulated by an upstream transmission/reception switch 118.

An image processing unit 119 generates an image from the measurement data. The image is displayed to a user using an operating console 120, and/or the image is stored in a storage unit 121. A central computer unit 122 controls the individual installation components.

In MR imaging, images with a high signal-to-noise ratio (SNR) may be recorded using local coils (e.g., coils). The local coils are antenna systems that are attached in the direct vicinity on (e.g., anterior) or under (e.g., posterior) the patient. During an MR measurement, the excited nuclei induce a voltage in the individual antennas of the local coil. The induced voltage is then amplified using a low-noise preamplifier (e.g., LNA, preamp) and transmitted by cables to the reception electronics. In order to improve the signalto-noise ratio even in the case of high resolution images, high-field installations (e.g., 1.5 T to 12 T and more) are used. Since more individual antennas may be connected to an MRI reception system than receivers are available, a switching matrix (e.g., RCCS), for example, is installed between reception antennas and receivers. The matrix routes the currently active reception channels (e.g., the reception channels that currently lie in the field of view of the magnet) to the available receivers. As a result, more local coil elements than receivers are available may be connected because, in the case of a whole body cover, local coils that are situated in the FoV or in a homogeneous volume of the magnet may be read out.

By way of example, an antenna system that may include one or more antenna elements (e.g., coil elements; array coil) is referred to as "coil" or "local coil". These individual antenna elements may be embodied as loop antennas (e.g., loops), butterfly coils or saddle coils. A local coil includes the coil elements, the preamplifier, further electronics (e.g., standing wave traps) and wiring, the housing and may include a cable with plug, by which the local coil is connected to the MR installation. A receiver (e.g., RX) attached to the installation side filters and digitizes signals received from the local coil and transmits the data to the digital signal processing device. The digital signal processing device may derive an image or spectrum from the measurement and makes the image or spectrum available to the user for the diagnosis.

Figure 2:
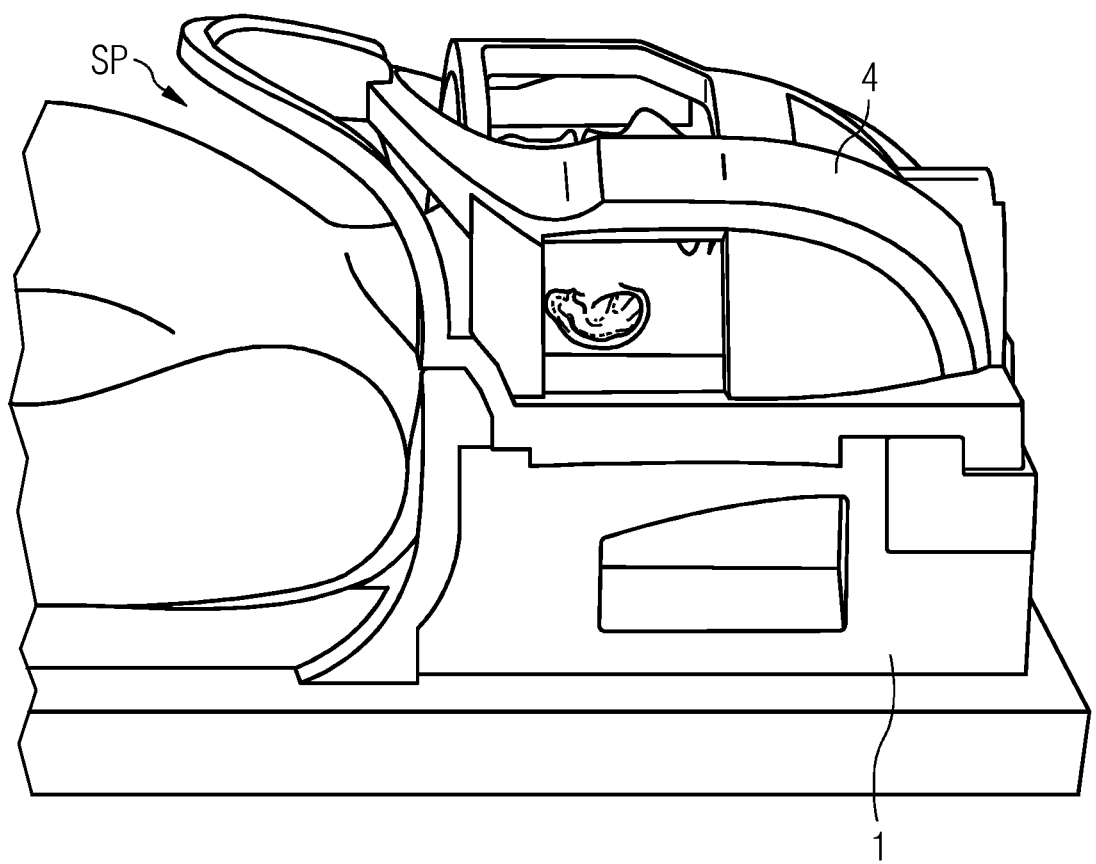
Figure 3:
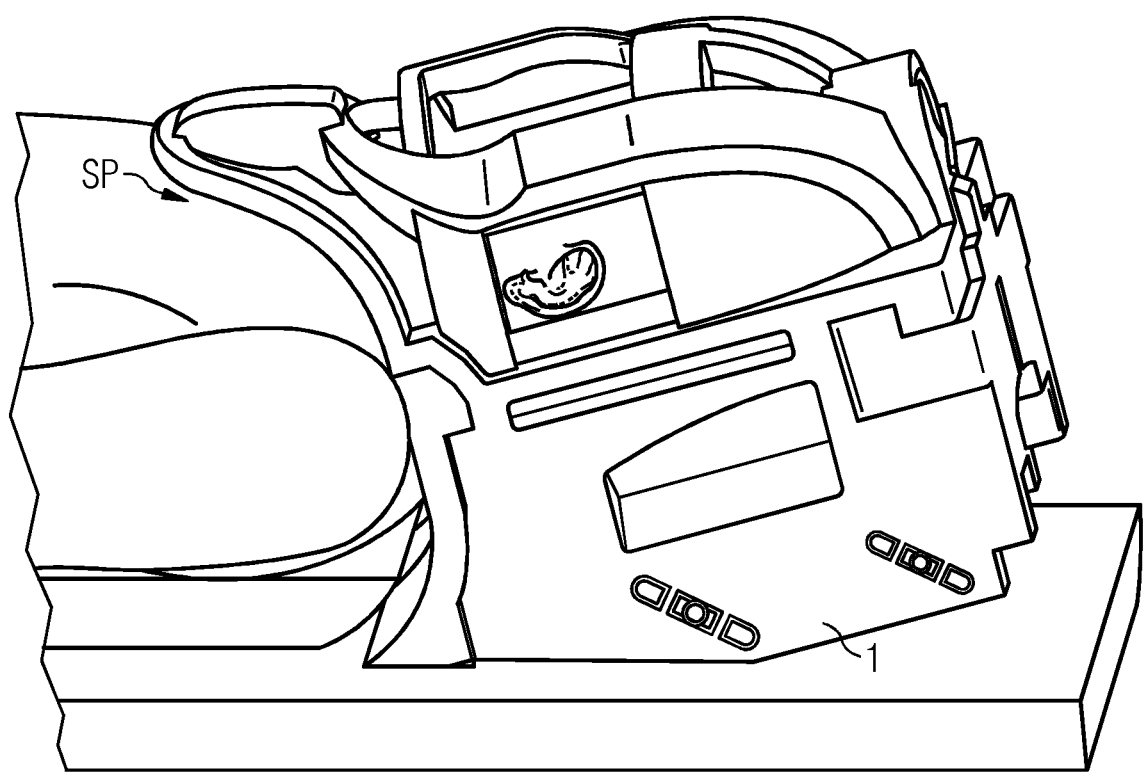
Figure 4:
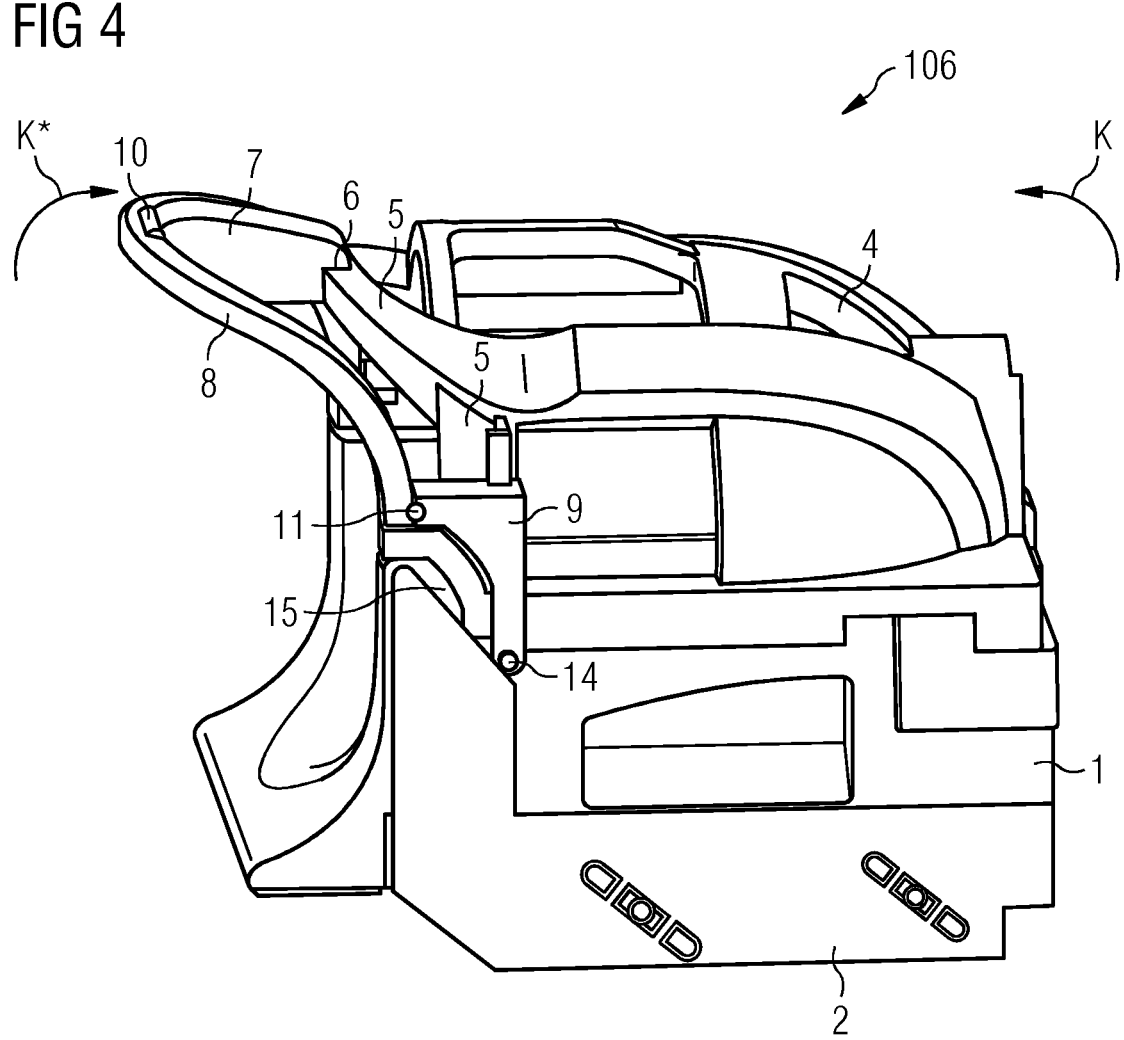
FIG. 4 shows, in a perspective drawing, a side view of one embodiment of a head/neck local coil in a non-tilted state.
Figure 5:
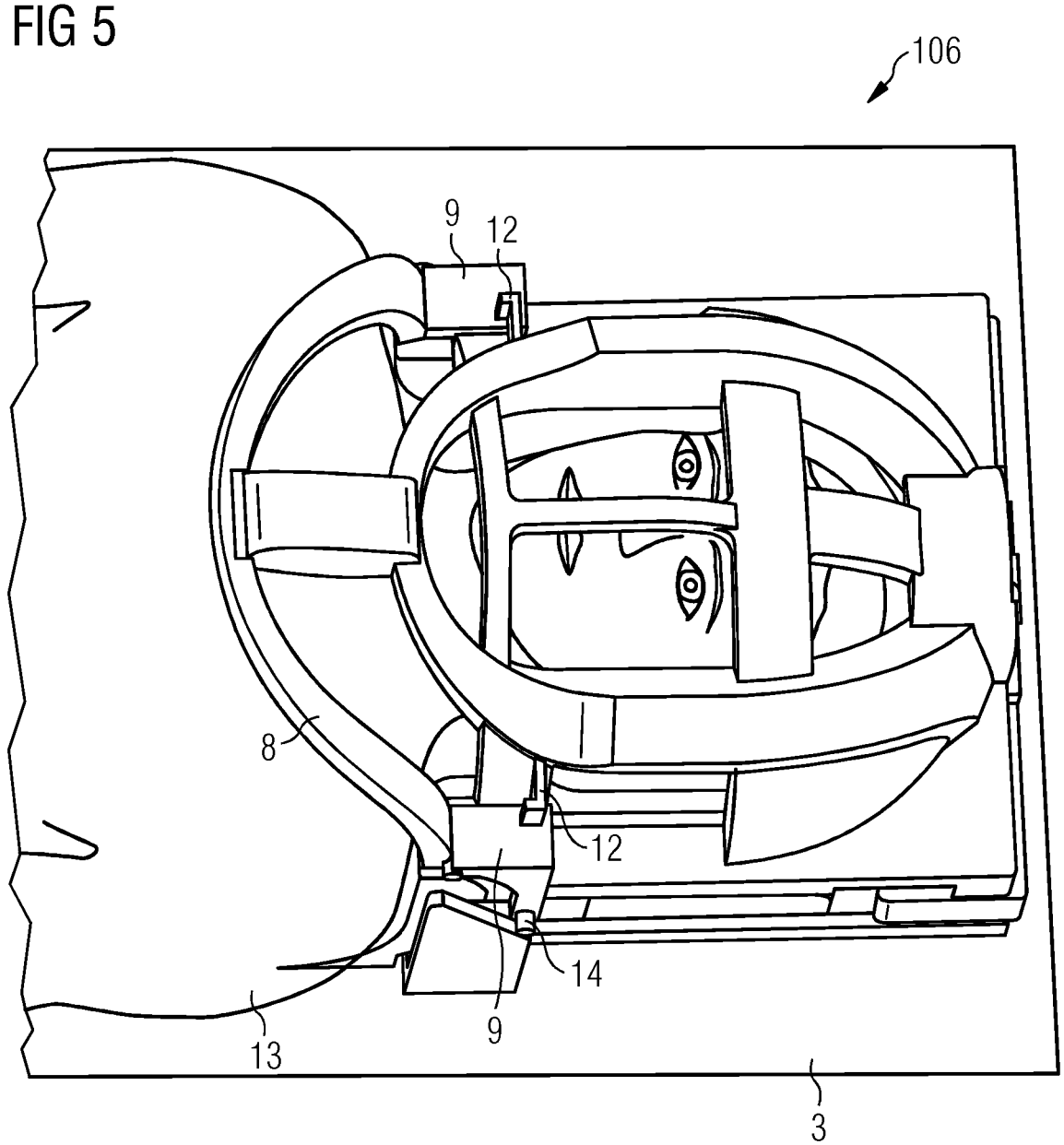
FIG. 5 shows, in a perspective drawing, a top view of one embodiment of a head/neck local coil in a non-tilted state.
Figure 6:
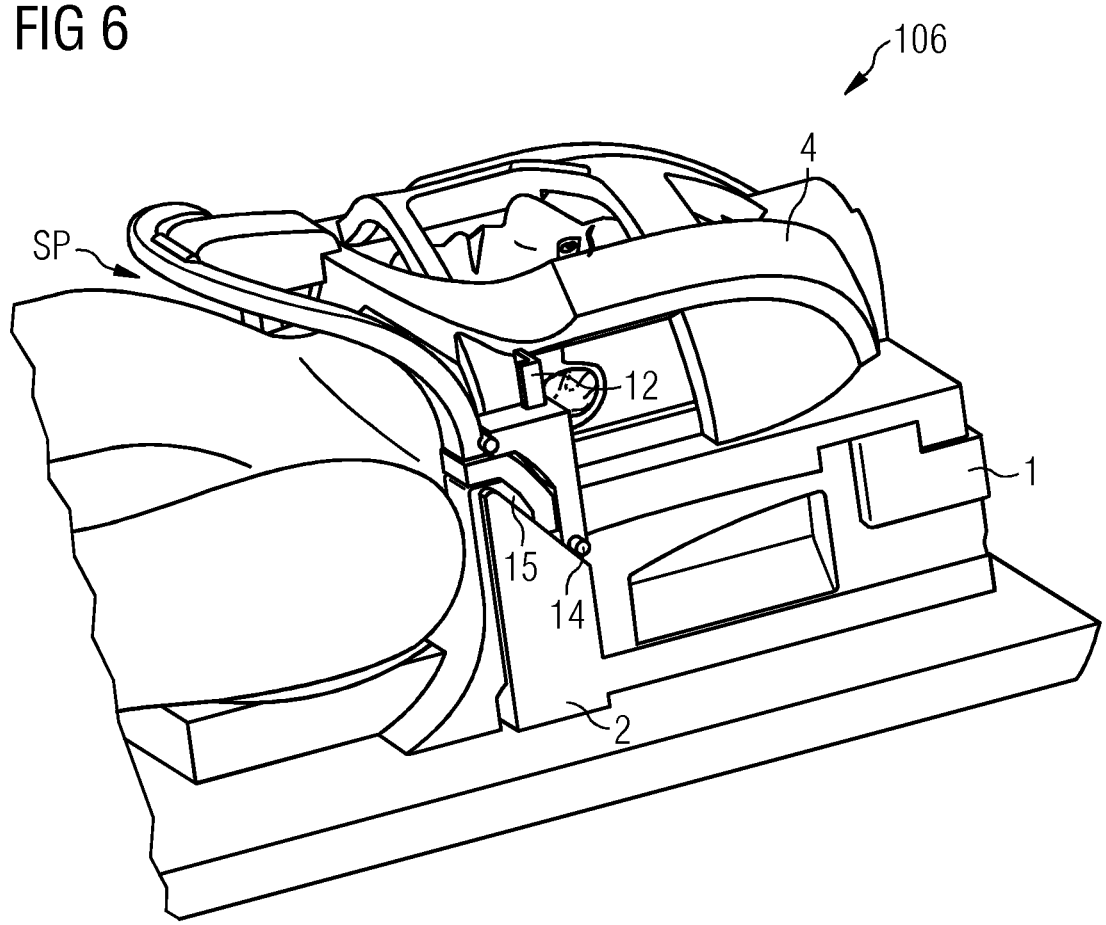
FIG. 6 shows, in a perspective drawing, a side view of one embodiment of a head/neck local coil with a patient in the head/neck local coil, in a non-tilted, flat state.
Figure 7:
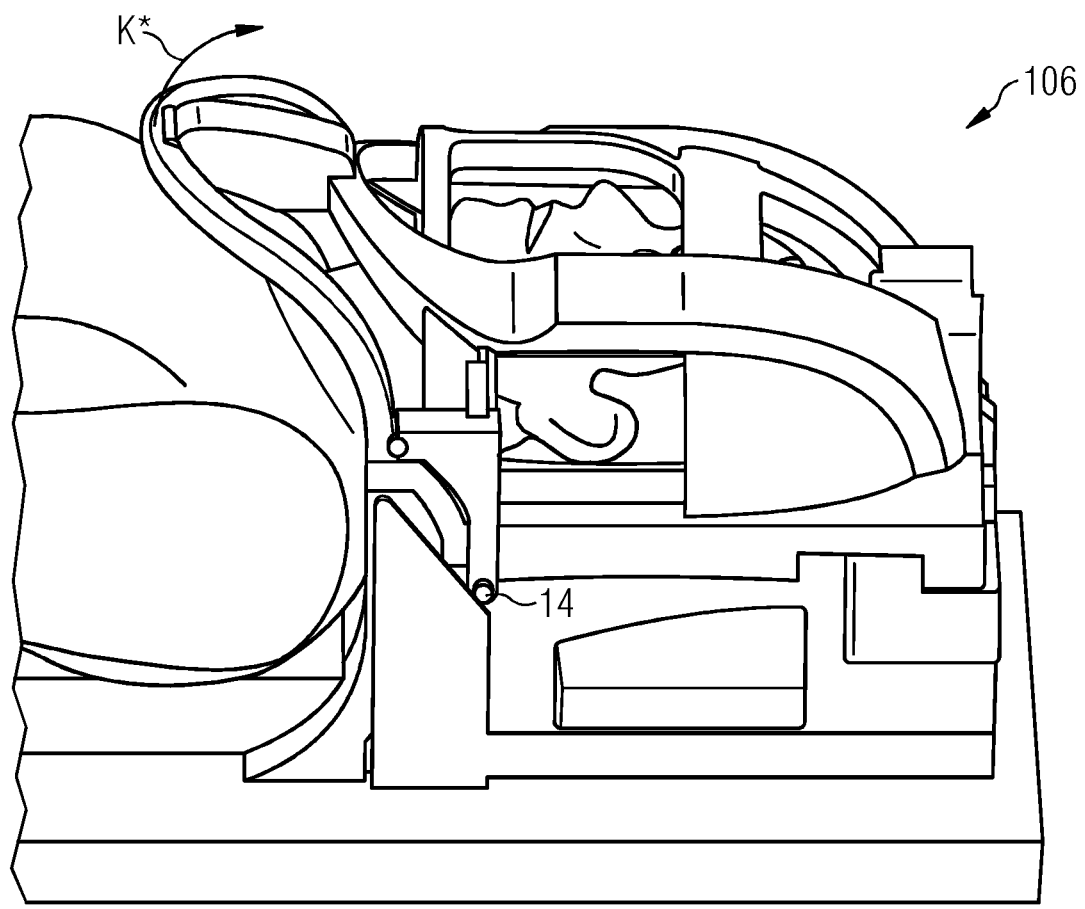
FIG. 7 shows, in a perspective drawing, a side view of one embodiment of a head/neck local coil with a patient in the head/neck local coil, in a non-tilted flat state.
Figure 8:
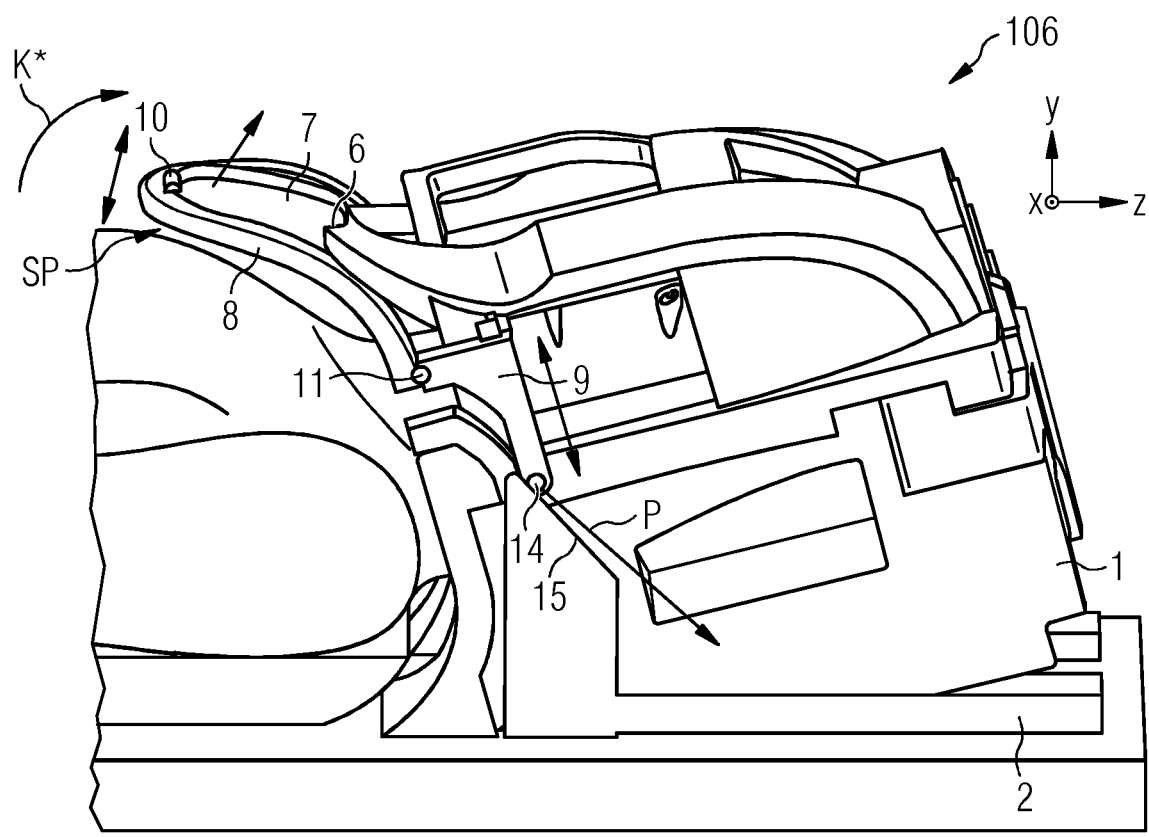
FIG. 8 shows, in a perspective drawing, a side view of one embodiment of a head/neck local coil with a patient in the head/neck local coil, in a tilted oblique state.
Figure 9:
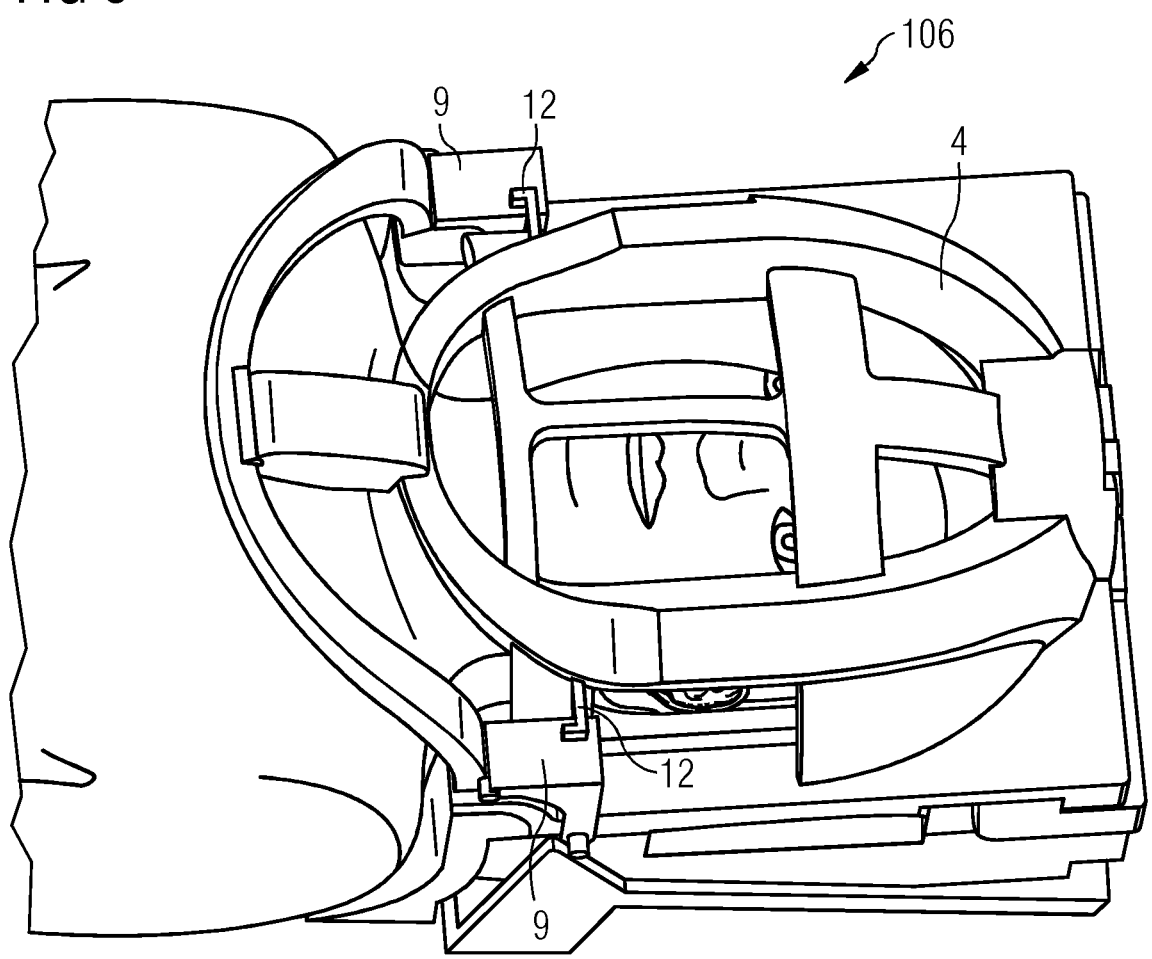
FIG. 9 shows, in a perspective drawing, a top view of one embodiment of a head/neck local coil with a patient in the head/neck local coil, in a tilted oblique state.
Figure 10:
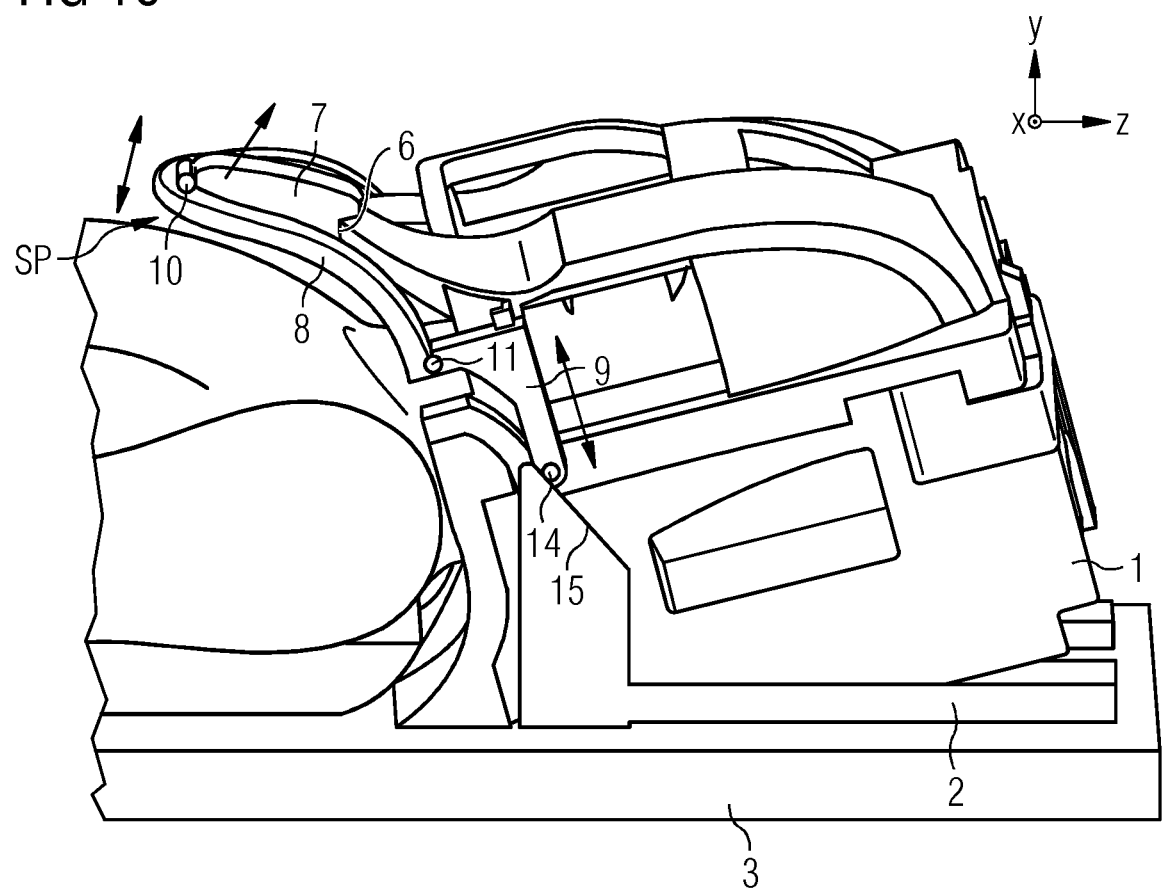
FIG. 10 shows, in a perspective drawing, a side view of one embodiment of a head/neck local coil with a patient in the head/neck local coil.

Head coils or combined head/neck local coils are embodied in a tiltable manner for improving the patient comfort or for supporting patients with pathological changes of the cervical spine (e.g., ankylosing spondylitis, torticollis, etc.). As a result of this, a gap SP between the chest of a patient and a strap of the head/neck local coil (e.g., from the position in FIG. 2 to the position in FIG. 3) may reduce, and the contour (e.g., a strap) of the neck coil may collide with the chest of the patient or restrict the freedom of movement of the chest. In order to rest close to the patient, high channel head/neck coils have small dimensions, which may promote collisions at this point or restrictions in the freedom of movement.

Figure 1:
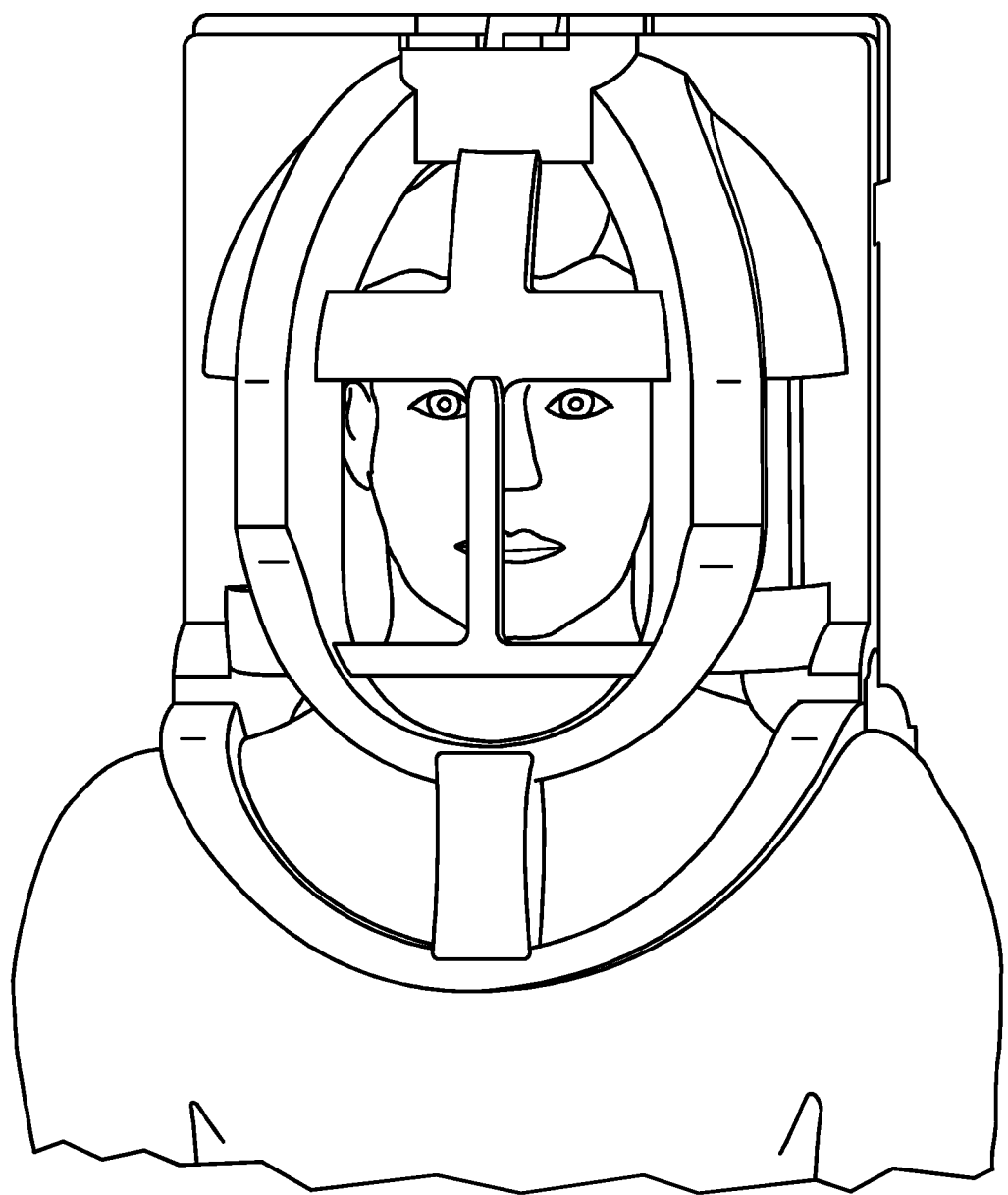
FIGS. 1-3 show a head/neck local coil.

A head/neck local coil (e.g., as depicted in FIG. 1 in a top view, in FIG. 2 in a non-tilted state in a side view, and in FIG. 3 in a tilted state in a side view) may not be tilted or may only be tilted a little. Known flexible neck coils may also have a movable flexible flap that may only have partial neck covering, and the position of the flexible flap may be reproducible to a restricted extent in a plurality of measurements that are offset in time. The flexible flaps may rest against the patient and may be moved by the patient. Respiratory and body movements may directly influence a generated image.

FIGS. 4 to 10 illustrate details of exemplary embodiments of head/neck local coils according to one or more of the present embodiments (e.g., local coils enabling an MRI examination of head and neck of a patient).

The following text describes a combined head/neck local coil 106 that includes a rigid height-adjustable neck part 5 and a movable neck part 7, 8, 9 (e.g., with a strap 8 remaining at approximately constant height y).

The rigid (e.g., inherently rigid), height adjustable neck part (e.g., also the movable neck part; the strap 8 of the movable neck part) is automatically adjusted (K*) (e.g., in the vertical direction y, for compensating the tilting movement K) when the head/neck local coil is tilted (K).

By way of example, the head/neck local coil 106 may be a "directly plugged" local coil 106, because the local coil 106 is directly plugged into a patient table 3 (e.g., by plugging the connector of the local coil 106 into a plug or a socket on the patient table 3).

The patent application DE 10 2011 079 565.0 describes how a directly plugged local coil may be tilted despite a mechanically secured connection to a patient table (e.g., fixed in terms of a position on the patient table).

A head/neck local coil 106, as is shown in FIGS. 4-10 (e.g., in perspective drawings in lateral views and in top views, and also in a tilted and non-tilted state), includes, for example, a head/neck local coil lower part 1 that is tiltable (e.g., in relation to a base lower part 2) and the base lower part 2, which may be placed onto a patient couch 3. The base lower part 2 establishes electrical contact with the patient couch 3 when directly plugging the local coil 106.

The head/neck local coil lower part 1, which may be tiltable by a tilting movement (e.g., as indicated by the arrow K), and the base lower part 2 are movable in relation to one another and thereby generate tilting of the local coil (e.g., with respect to a description and exemplary embodiments, see also U.S. Patent Application Publication No. 20130184563, which is hereby incorporated by reference in its entirety). The local coil 106 includes a head upper part 4, which, for example, also includes a part 5 of the neck coil that is immobile in relation to the head upper part 4 (e.g., the part 5 of the neck coil that is stationary in relation to the head upper part 4). The movable neck part 7, 8, 9 of the neck coil is attached to the stationary neck part 5 (e.g., optionally also with antennas for imaging the neck). The movable neck part 7, 8, 9 includes a plurality of rigid parts that are mounted in a rotatable manner with respect to one another; in this case, this includes a tilting part 7, a rigid strap 8 and pushing parts 9. All or individual ones of these parts 7, 8, 9 may in each case include antenna elements and/or electronic components. The tilting part 7 is mounted in a rotatable manner on the immobile part 5 of the neck coil by a rotary joint 6. The rigid neck strap 8 is mounted in a rotatable manner on the tilting part 7 by the rotary joint 10. The lower ends of the rigid neck strap 8 are, on both sides of the local coil 106, connected in a rotatable manner to the pushing parts using the rotary joints 11. The pushing parts 9 may move (e.g., vertically) along the linear guide 12, which is fastened to the stationary neck part 5 and hence also to the head upper part 4 (e.g., the head receiving part of the local coil 106, in which a head KO of a patient is intended to be situated).

In order to prepare an MRI examination, the base lower part 2 is positioned on the patient couch 3. A patient 13 is placed in the local coil 106, which may already be tilted (e.g., as in FIGS. 8-10) or may be non-tilted (as in FIGS. 4-7). The local coil 106 may remain flat (e.g., non-tilted) on the patient couch 3 in the case of most patients 13. If patients 13 who cannot, for various reasons, place their head KO flat into the local coil 106 are examined, the head/neck local coil lower part 1 (or a part of the head/neck local coil lower part 1 and the immobile and movable neck parts 7, 8, 9 together) may be tilted before laying down the patients 13. However, the head/neck local coil lower part 1 may also be tilted with patients 13.

Thus, at the moment when the complete upper part 4-9 of the local coil 106 is put on, the head/neck local coil lower part 1 may be tilted (e.g., K, FIGS. 8-10) or non-tilted (e.g., FIGS. 4-7). In order to automatically move the movable neck strap 8 away from the patient 13 in the tilted state of the head/neck local coil lower part 1, each of the pushing parts 9 includes a stud 14. If the complete local coil upper part (e.g., element 4, elements 4-9) is placed onto the head/neck local coil lower part 1, the studs 14 are incident on both sides on the guide edges 15 that are integrated in the immobile base lower part 2. The studs 14 are displaced along the guide edges 15 (e.g., in the direction of the arrow P) depending on the tilting angle (e.g., in the direction K) of the local coil. The studs 14 transmit the movement to the pushing parts 9, which are pressed upward on the linear guides 12. The pushing parts 9 likewise push the rigid neck strap 8, mounted thereon in a rotatable manner by the rotary joints 11, upward. Within the scope of this movement, the tilting part 7, mounted by the rotary joints (e.g., elements 6 and 10, on both sides on the tilting part 7), is likewise tilted upward (e.g., in the direction of the arrow and the y-axis). As a result of this mechanism, the tilting movement of the part 1 of the head coil is directly transmitted (e.g., in the opposite direction) onto the neck strap 8. The tilting K of the head coil may be continuous, where the neck coil may open together with each degree of the tilting of the head/neck local coil lower part 1.

In the case of slim patients 13 who are positioned in the tilted head/neck local coil 106, a flat chest may not require enlargement of the neck coil despite the local coil tilt K because sufficient space is still available between the patient and neck strap 8. In this case, the automatic coupling of the tilting movements "may be switched off": the studs 14 on the pushing parts 9 include a compression spring and latch into the pushing parts 9 in an interlocking manner as a result of pressure and a slight rotation (e.g., approximately 10°). In the latched state, the studs 14 no longer protrude and do not impact on the guide edges 15 when putting on the complete local coil upper part 4-9. Therefore, the described mechanism for adjusting the size of the neck part 7, 8, 9 (e.g., by tilting the strap 8 is not activated. For unlocking purposes, the studs 14 are slightly rotated, the interlock disengages, and the compression springs press the studs 14 out again. By way of example, this process is only possible, for example, in the non-tilted initial position (e.g., as in FIGS. 4-7) of the head/neck local coil lower part 1 when the upper part is placed on the head/neck local coil lower part 1 (e.g., with/without 4-9) or possible at any time on the separate upper part 4 (e.g., not placed onto the head/neck local coil lower part 1).

Thus, an embodiment relates to a head/neck local coil 106 with a tilting function (K) and an automatically coupled (e.g., by tilting K* at least one strap 8 opposite to the tilting direction K of the upper part for compensating the upper part) and/or size-adjustable neck coil part (e.g., elements 7, 8, 9). An enlargement of the neck opening (e.g., in the form of a gap SP between patient and strap 8) of the local coil 106 may allow for a larger clear space for the patient (e.g., gap SP).

Subdividing the neck coil into rigid parts (e.g., elements 5, 7, 8 and 9) that are mounted in a rotatable manner with respect to one another using rotary joints (e.g., elements 6, 10 and 11) allows the implementation of a geometrically constant connection (e.g., of the strap at the constant position thereof) to the head coil (e.g., element decoupling).

The neck coil may be dimensioned such that there is no contact between the strap 8 of the neck coil and the patient 13 in the non-tilted initial position (e.g., in accordance with FIGS. 4-7) so that no movement artifacts are caused.

Direct coupling of the tilting movement K of the head/neck local coil lower part 1 with the movable neck coil (e.g., with a tilting movement K* on the movable neck coil) may be provided.

A drive of the movement of the neck strap 8 may be provided by studs 14 and guide edges 15.

Continuous setting of the movement may be provided.

Spring-mounted pickup studs 14 may "switch off" the coupling between the movements via the studs being pressed and latched in.

Preventing a collision between patient and neck coil in the tilted state of the head/neck local coil may avoid movement artifacts during an imaging MRI measurement.

An advantage may lie in good reproducibility of examinations by a coupled movement.

The guide length of the linear guide of 12 with the pushing parts 9 may be dimensioned such that there is freedom from jamming.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A head and neck local coil for a magnetic resonance imaging system, the head and neck local coil comprising:
    a base lower part;
    a head and neck local coil lower part that is tiltable with a tilting movement relative to the base lower part;
    a head upper part supportable on the head and neck local coil lower part; and
    a neck part movable relative to the head and neck local coil lower part for compensating the tilting movement, the neck part comprising pushing parts, each of the pushing parts having a stud provided to automatically reduce or avoid a space between a movable neck strap and a patient when the head and neck local coil lower part is tilted,
    wherein the head upper part comprises a first neck part and a second neck part, the second neck part being movable relative to the first neck part and being fastened to the first neck part, and
    wherein when the head upper part is supported on the head and neck local coil lower part, the studs are displaceable on guide edges of the base lower part.

2. The head and neck local coil of claim 1, wherein the neck part is a first neck part, and wherein the head and neck local coil further comprises a second neck part, the first neck part and the second neck part being movable relative to one another.

3. The head and neck local coil of claim 1, wherein the movable neck part comprises a plurality of rigid parts that are mounted in a rotatable manner with respect to one another.

4. The head and neck local coil of claim 3, wherein the plurality of rigid parts comprises a tilting part, the movable neck strap, or a combination thereof.

5. The head and neck local coil of claim 1, wherein the movable neck part comprises a plurality of rigid parts, one or more rigid parts of the plurality of rigid parts comprising one or more antenna elements.

6. The head and neck local coil of claim 1, wherein the movable neck part comprises the movable neck strap having at least one antenna in the movable neck strap, the movable neck strap being positioned above a neck, a chest, or the neck and the chest of a patient.

7. The head and neck local coil of claim 1, wherein the movable neck part comprises a tilting part, the tilting part being mounted via a rotary joint in a rotatable manner on the immobile first neck part, and
wherein the movable neck strap is rigid and mounted in a rotatable manner over the rotary joint on the tilting part.

8. The head and neck local coil of claim 7, wherein lower ends of the movable neck strap are in each case connected in a rotatable manner to one of the pushing parts via rotary joints on both sides of the head and neck local coil.

9. The head and neck local coil of claim 1, wherein the pushing parts are movable in one direction with a vertical component along a linear guide that is fastened to the first neck part and to the head upper part.

10. The head and neck local coil of claim 1, wherein the studs are displaceable along the guide edges depending on a tilt angle of the head and neck local coil lower part with respect to the base lower part.

11. The head and neck local coil of claim 1, wherein the studs on the pushing parts are configured to press the pushing parts vertically upward on linear guides when tilting the head and neck local coil lower part relative to a base lower part such that the pushing parts press the movable neck strap, mounted thereon in a rotatable manner via rotary joints, upward.

12. The head and neck local coil of claim 11, wherein the studs on the pushing parts comprise a compression spring, and
wherein the studs are latchable into the pushing parts in an interlocking manner.

13. The head and neck local coil of claim 11, wherein, when the studs are latched in an interlocking manner, the studs are positioned such that the studs do not rest on guide edges integrated in the base lower part when the local coil upper part is placed onto the base lower part, the studs do not engage with the guide edges integrated in the base lower part when the local coil upper part is placed onto the base lower part, or a combination thereof.

14. The head and neck local coil of claim 1, wherein the tilting movement causes an automatic movement of the movable neck strap, and
wherein the automatic movement of the movable neck strap is deactivatable by further tilting movements of the head and neck local coil lower part relative to a base lower part.

15. The head and neck local coil of claim 1, wherein the head and neck local coil lower part relative to a base lower part is tiltable in a continuous manner.

16. The head and neck local coil of claim 1, wherein the head and neck local coil is a head and neck local coil for magnetic resonance imaging of the head and for magnetic resonance imaging of the neck of the patient.

17. The head and neck local coil of claim 1, wherein the neck part comprises the movable neck strap that is movable relative to the head and neck local coil lower part at least in a vertical direction for complete or partial compensation of a tilting movement of the head and neck local coil lower part.

18. The head and neck local coil of claim 1, wherein the neck part is automatically movable for automatic compensation of the tilting movement of the head and neck local coil lower part.

* * * * *